United States Patent
Lee et al.

(10) Patent No.: US 10,531,937 B2
(45) Date of Patent: Jan. 14, 2020

(54) DENTAL IMPLANT SYSTEM WITH POSITIVE ABUTMENT SCREW LOCKING AND RETRIEVAL MECHANISM

(71) Applicants: Chi Keung Lee, Palo Alto, CA (US); Gurpreet Singh Narula, San Jose, CA (US)

(72) Inventors: Chi Keung Lee, Palo Alto, CA (US); Gurpreet Singh Narula, San Jose, CA (US)

( * ) Notice: Subject to any disclaimer, the term of this patent is extended or adjusted under 35 U.S.C. 154(b) by 50 days.

(21) Appl. No.: 16/062,406

(22) PCT Filed: Oct. 25, 2017

(86) PCT No.: PCT/US2017/058363
§ 371 (c)(1),
(2) Date: Jun. 14, 2018

(87) PCT Pub. No.: WO2018/081312
PCT Pub. Date: May 3, 2018

(65) Prior Publication Data
US 2018/0368951 A1 Dec. 27, 2018

Related U.S. Application Data

(60) Provisional application No. 62/412,547, filed on Oct. 25, 2016.

(51) Int. Cl.
*A61C 8/00* (2006.01)

(52) U.S. Cl.
CPC .......... *A61C 8/0068* (2013.01); *A61C 8/0074* (2013.01); *A61C 8/0089* (2013.01); *A61C 8/0022* (2013.01); *A61C 8/0093* (2013.01)

(58) Field of Classification Search
CPC ....... A61C 8/0068; A61C 8/005; A61C 8/006; A61C 8/0063; A61C 8/0074; A61C 8/0089
See application file for complete search history.

(56) References Cited

U.S. PATENT DOCUMENTS

| | | | | |
|---|---|---|---|---|
| 5,125,840 A | * | 6/1992 | Durr | A61C 8/005 433/173 |
| 5,704,788 A | * | 1/1998 | Milne | A61C 8/005 433/172 |

(Continued)

FOREIGN PATENT DOCUMENTS

| WO | WO 02/055404 A1 | * | 7/2003 |
| WO | WO 2006/116652 A2 | * | 11/2006 |

OTHER PUBLICATIONS

International Search report dated Jan. 3, 2018 in corresponding PCT Application No. PCT/2017/058363 filed Oct. 25, 2017.

(Continued)

*Primary Examiner* — Ralph A Lewis
(74) *Attorney, Agent, or Firm* — Thomas | Horstemeyer, LLP

(57) ABSTRACT

A new dental implant system with positive abutment screw locking and retrieval mechanisms is provided. The abutment screw is positively locked by a keying pin to improve fatigue life. The abutment screw is also equipped with a special feature that greatly improves the retrievability of the broken screw from inside the implant. In addition, the keying pin is designed with a lock nut as a sub-assembly for ease of installation.

20 Claims, 3 Drawing Sheets

(56) References Cited

U.S. PATENT DOCUMENTS

| | | | | |
|---|---|---|---|---|
| 5,733,122 | A * | 3/1998 | Gordon | A61C 8/005 433/172 |
| 5,782,918 | A * | 7/1998 | Klardie | A61C 8/005 433/172 |
| 6,857,874 | B2 * | 2/2005 | Kim | A61C 8/005 433/172 |
| 8,740,615 | B2 * | 6/2014 | Ishiwata | A61C 8/0066 433/173 |
| 2005/0256540 | A1 * | 11/2005 | Silver | A61C 8/00 607/3 |
| 2008/0227058 | A1 | 9/2008 | Karmon | |
| 2013/0224689 | A1 | 8/2013 | Ishiwata | |
| 2014/0205969 | A1 | 7/2014 | Marlin | |
| 2016/0206409 | A1 * | 7/2016 | Kim | A61C 8/0078 |
| 2016/0302893 | A1 | 10/2016 | Vukas | |
| 2018/0008380 | A1 * | 1/2018 | Lee | A61C 8/0012 |
| 2018/0368951 | A1 * | 12/2018 | Lee | A61C 8/006 |

OTHER PUBLICATIONS

PCT Written Opinion dated Apr. 30, 2019 in copending PCT/US2017/058363 filed Oct. 25, 2017.

\* cited by examiner

DENTAL IMPLANT SYSTEM WITH POSITIVE ABUTMENT SCREW LOCKING AND RETRIEVAL MECHANISM

CROSS-REFERENCE TO RELATED APPLICATIONS AND PRIORITY CLAIM

This application is a PCT international application that claims priority to, and the benefit of the filing date of, a U.S. provisional application having application Ser. No. 62/412,547, filed on Oct. 25, 2016, entitled "DENTAL IMPLANT SYSTEM WITH POSITIVE ABUTMENT SCREW LOCKING AND RETRIEVAL MECHANISMS," which is incorporated by reference herein in its entirety.

TECHNICAL FIELD OF THE INVENTION

The invention relates to a dental implant system with high mechanical performance and serviceability. More importantly, the invention relates to an abutment screw design with positive locking and retrieval mechanisms for improving the screw fatigue life and for allowing easy retrieval of a broken abutment screw remnant inside the implant in the event that the abutment screw breaks.

BACKGROUND OF THE INVENTION

Dental implant technology is a mature technology that is becoming increasingly affordable and popular. This is a second line of defense apart from the root canal procedure with a cemented crown.

The common titanium alloy dental implant system consists of an implant that goes into the jaw bone, a titanium alloy abutment, a titanium alloy abutment screw, and a zirconia cemented crown or screw-retained cemented crown.

The success of a dental implant depends on many factors. Some patients do not have sufficient bone after extraction of the tooth, and therefore will require grafting, a type of artificial bone matrix that can be fused with the jaw bone. Pilot tap drills are used to prepare for the implant installation. The general design of an implant has a threaded outside profile and internal threads for mating with the abutment screw. Some implant designs can achieve thread forming and therefore no tapping is required when preparing the drilled cavity for the implant installation. The implant will be screwed and secured into the jaw bone at or 1 millimeter (mm) to 2 mm below the crest of the bone.

A secure implant primary mechanical stability is critical for the success of the implant integration. Usually the patient has to wait for a few months to ensure a successful osseointegration, a biological bone growth process around the threaded implant. This is often referred to as the secondary stability. The implant with good secondary stability can withstand the occlusal loads of mastication on the crowned abutment.

For the cemented type crown, the abutment will be secured to the implant by the abutment screw followed by the crown cementation. The bonding of the cemented crown to the abutment with resin cement is generally non-permanent and therefore allows the crown to be removed from the abutment with the use of a special tool. The abutment screw will be screwed down at a prescribed torque value from the dental implant manufacturer. For the screw-retained cemented type crown, the crown is permanently fused onto the abutment. The screw-retained cemented crown has a small through hole that accepts the abutment screw into the abutment and secures the abutment to the implant. A small filling procedure will be administered to cover the small circular hole for functional and aesthetics purposes.

One of the major issues of the current implant system is that the abutment screw will become loose over time due to cyclic occlusal loads on the cemented crown or screw-retained cemented crown. The occlusal load has one vertical component and one lateral force component. The abutment screw will exhibit a normal fatigue failure life due to cyclic vertical loads on the crown. The cyclic lateral loads on the crown will cause a joint slip at the contact interface between the abutment screw and the abutment. This joint slip effect will reduce the prescribed torque on the abutment screw and cause it to self-loosen. Usually, at the very early stage of abutment screw self-loosening, a slight rotational movement of the crown is noticeable. The patient should then seek a dental appointment to re-torque the abutment screw. A delayed response will lead to further self-loosening of the abutment screw, bending loads, micro-crack propagation, and subsequent failing due to fatigue.

Another major issue is the retrieval of the broken abutment screw remnant inside of the implant. This is truly a well-known challenging and time consuming issue in the dental implant dentistry. Many dentists have used special tools or come up with their own custom tools in order to tackle this problem. As discussed in the previous section, the abutment screw will become loose and fail at some point in time due to fatigue. The location of breakage or fracture along the abutment screw will dictate the level of difficulty for accessibility and retrievability. Some abutment screws fail and sheer just below the screw head, but the remaining portion is visible and tool-accessible. Other abutment screws fail anywhere along the threaded length with limited visibility and tool accessibility. In addition, there is another risk of damaging the implant internal threads and making the implant non-usable when operating the special tools to retrieve the broken abutment screw.

Accordingly, a need exists for a new dental implant system to resolve the two major foregoing issues.

DETAILED DESCRIPTION OF AN EXEMPLARY EMBODIMENT

The inventive principles and concepts are directed to a new dental implant system design that resolves the aforementioned abutment screw self-loosening and broken abutment retrieval issues for single tooth cemented-type crown or single tooth screw-retained-type crown. The inventive principles and concepts also apply to bridge-type implants for multiple teeth and other dental implant applications, such as implant-supported prosthetics, for example.

The attachment of different crown types onto the abutment has been addressed and discussed previously. In the interest of brevity and for ease of discussion, the following discussion is focused on the mechanical aspects of the individual piece part only.

In accordance with a representative embodiment, the dental implant system comprises four major piece parts, excluding the crown to be cemented on or already fused onto the abutment. The major piece parts comprise one implant, one abutment, one abutment screw, and a sub-assembly of a lock nut with a keying pin. The sub-assembly is treated as a single piece part herein although in reality it comprises two piece parts. The four major piece parts may be made of a variety of biologically-compatible materials such as, for example, a titanium alloy or any other suitable biologically-compatible material having desired mechanical characteristics. The four major piece parts may be made by, for example, machining and/or metal injection molding with and without secondary machining operations. The dental implant system obviates the aforementioned self-loosening problem, thereby extending the screw fatigue life while also obviating the retrievability problem by allowing the abutment screw remnants to be easily retrieved in the event that the abutment screw is broken or otherwise fails.

Figure 2:
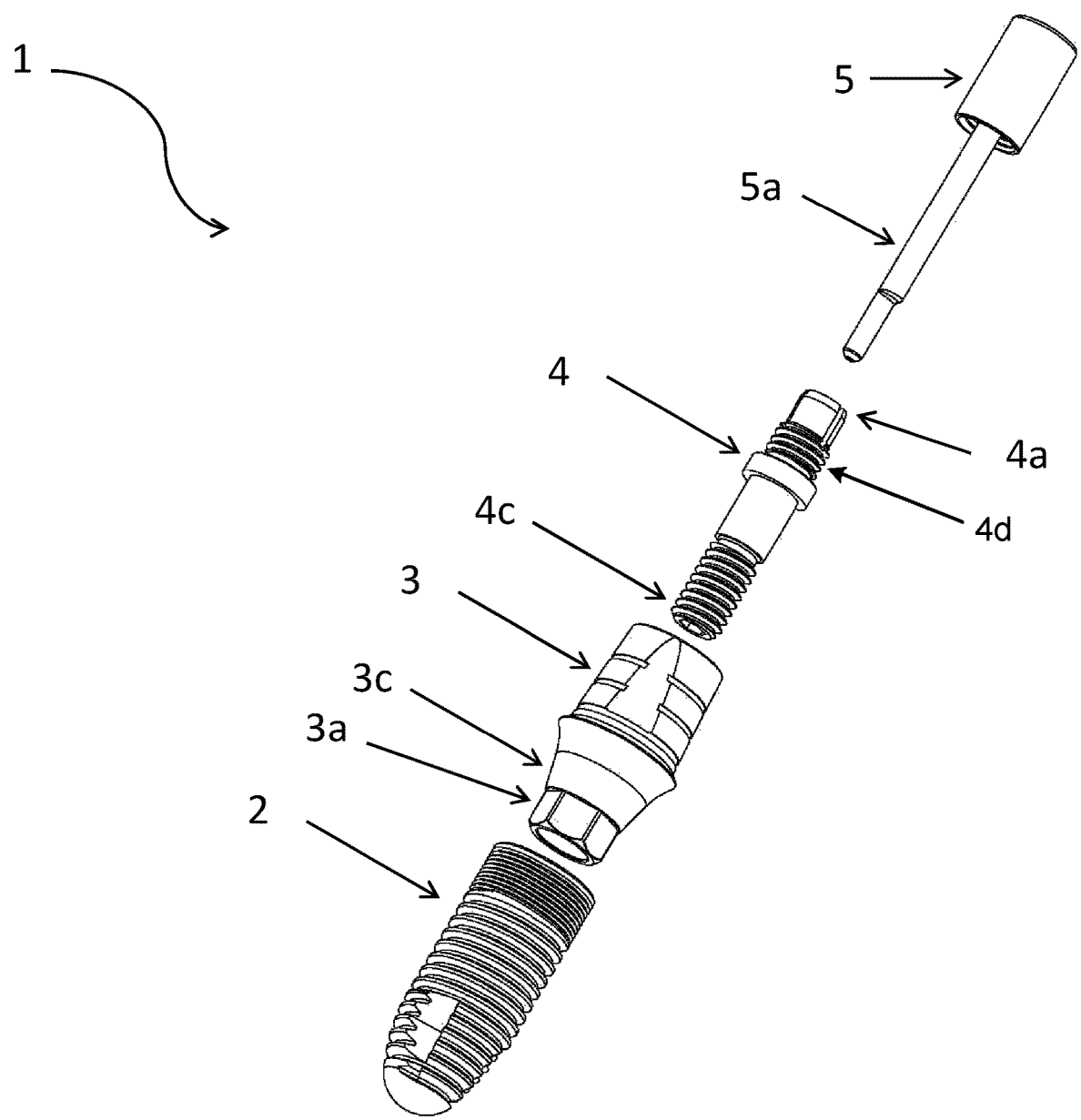
FIG. 2 illustrates a perspective exploded view of the dental implant system without the cemented crown or screw-retained cemented crown.
Figure 3:
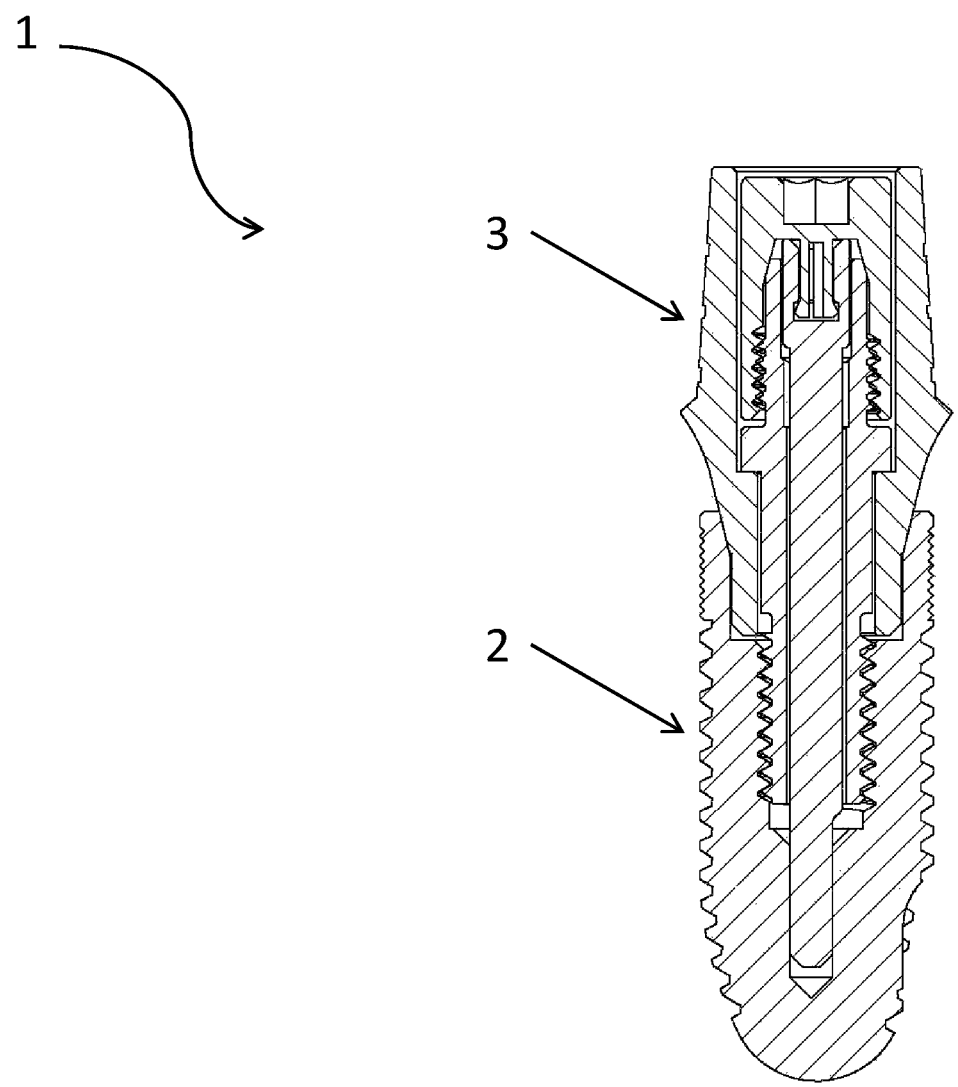
FIG. 3 illustrates a perspective cross-sectional view of the dental implant system without the cemented crown or screw-retained cemented crown.

Representative, or exemplary, embodiments will now be described with reference to FIGS. 1-3, in which like reference numerals identify like features, elements or components. It should be noted that features, elements or components shown in the drawings are not necessarily drawn to scale.

Figure 1:
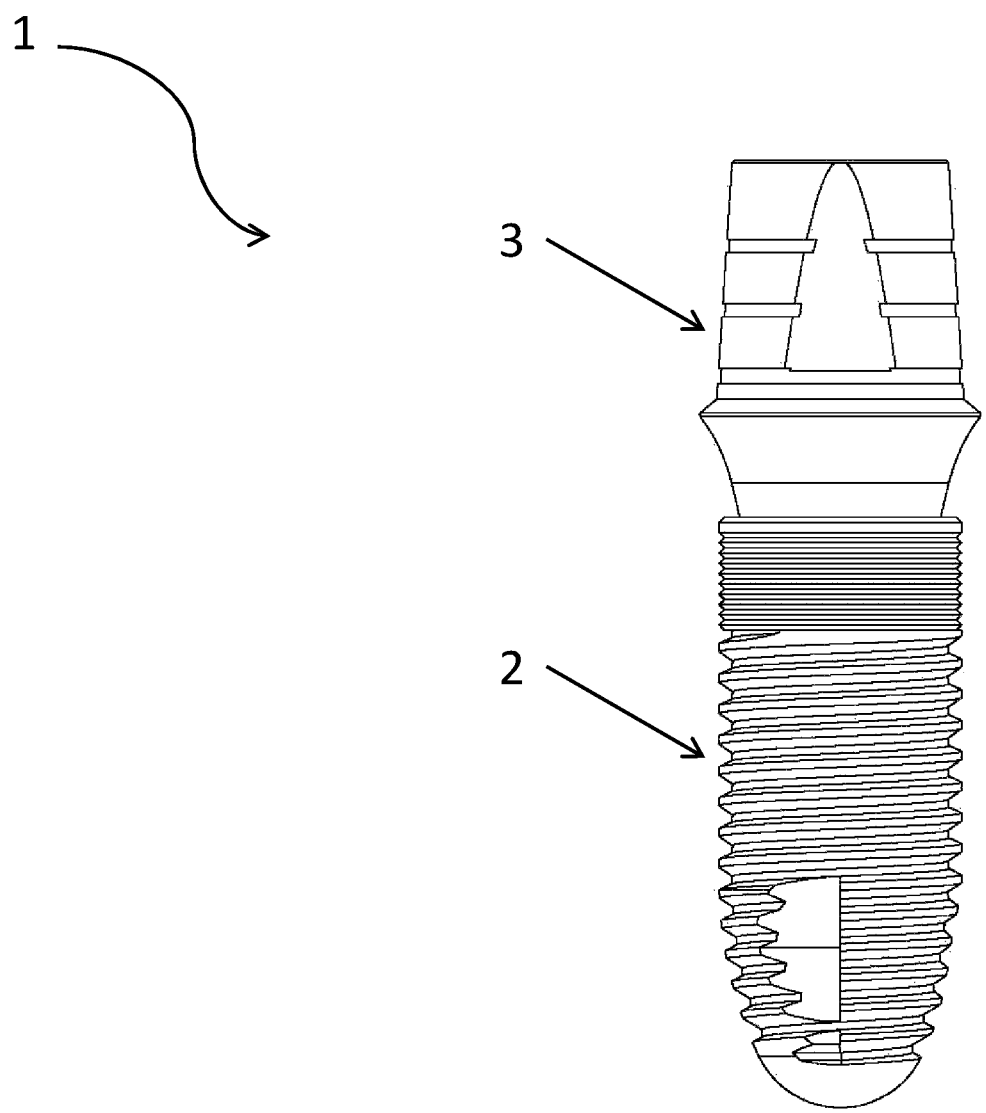
FIG. 1 illustrates a perspective view of the dental implant system without the cemented crown or screw-retained cemented crown.

FIG. 1 illustrates a perspective view of the dental implant system 1 in assembled configuration in accordance with a representative embodiment. For clarity, the cemented crown and screw-retained crown are not shown in FIG. 1. FIG. 2 illustrates a perspective exploded view of the dental implant system 1 without the cemented and screw-retained crown. FIG. 3 illustrates a perspective cross-sectional view of the dental implant system 1 without the cemented and screw-retained crown.

In the perspective view shown in FIG. 1, the abutment 3 is shown installed in the implant 2. In the perspective exploded view shown in FIG. 2, the piece parts of the dental implant system 1 are shown separately, including the implant 2, the abutment 3, the abutment screw 4 and the sub-assembly comprising the lock nut and keying pin 5 and 5a, respectively. FIG. 2 also shows the actual assembly sequence of the dental implant system 1. In the perspective cross-sectional view of the dental implant system 1 shown in FIG. 3, the piece parts shown in FIG. 2 are assembled together.

As discussed above in the Background, an implant having successful secondary stability inside of the jaw bone is ready for the abutment to be installed with the use of an abutment screw. The inventive principles and concepts are also directed to an assembly method that is generally the same as the known assembly method described above in the Background except that the assembly method in accordance with the inventive principles and concepts includes a step of installing the lock nut 5 and keying pin 5a of the sub-assembly onto the abutment screw 4.

The dental implant system 1 in accordance with the representative embodiments has unique features in each of the individual piece parts, which will now be described with reference to the representative, or exemplary, embodiment. The implant 2 has a female Morse Taper cavity that enables a tight fit or interference fit with a Morse Taper male portion 3c of the abutment 3 when tightening the abutment screw 4. The Morse Taper feature restrains the abutment 3 from axial and rotational movements relative to the implant 2. Additionally, the Morse Taper feature provides a hermetic seal that is ideally maintained throughout the life time of the abutment screw 4 to prevent growth of bacteria at the crevice between the implant 2 and the abutment 3. The implant 2 also includes a hex socket cavity that mates with the hex head 3a disposed on the end of the abutment 3 to handle the excessive torsional load from the Morse Taper interface to the interface of the implant hex socket cavity and the hex head 3a of the abutment 3. The implant hex socket cavity serves as a hard stop to further retrain rotational motion of the abutment 3 relative to the implant 2.

The installation of the implant 2 into the pre-drilled jaw bone cavity may be achieved by using a standard Allen key or hex head screwdriver to screw the implant 2 into the jaw bone. The implant 2 is equipped with a tap drill hole having internal threads that are adapted to mate with external threads of the abutment screw 4. There is an internal chamfer feature below the internal threads of the tap drill hole and a small circular blind cavity under the chamfer. The centerline of the blind cavity is off-centered with respect to the internal chamfer feature of the implant 2 and with respect to the tap drill hole. The off-centered internal chamfer feature provides a guiding surface for the tip of the keying pin 5a to achieve blind-mating with the small circular blind cavity of the implant 2. The blind-mating action of the keying pin 5a includes self-rotating and a vertical linear motion when the lock nut 5 is being pushed down by an Allen key or hex head screwdriver. The engagement of the blind-mated portion of the keying pin 5a with the blind cavity of the implant 2 is a free-running fit.

The hex head 3a of the abutment 3 mates with the hex socket cavity of the implant 2 with a tight tolerance that minimizes lateral and rotational motions of the abutment 3 relative to the implant 2. There is also a flat ring shape surface on the hex head 3a that abuts a flat ring shape surface of the implant 2 to provide a reliable mechanical seal between these abutting surfaces. These abutting surfaces restrain relative movement between the implant 2 and the abutment 3 in the seated, or assembled, position. The abutment 3 has a through hole and a hard stop for engaging the abutment screw 4.

The abutment screw 4 is hollow inside with one small hex through slot 4c and one slightly larger blind hex slot. The abutment screw 4 has an exterior profile with a threaded bottom portion that allows mating with the internal threads of the implant 2. The small hex through slot 4c is important to resolving the aforementioned second major dental implant issue, namely, retrieval of the broken abutment screw remnant from inside of the implant. Unlike the conventional abutment screw design with a solid cross section along the entire screw length, the hex through slot keying feature allows the broken portion to be easily removed from the implant 2 by using a simple hand tool such as Allen key or hex head screwdriver. This unique feature enables successful broken abutment screw retrievals to be performed regardless of the breakage or fractured location along the screw 4. The retrieval operation is simple and straight forward and is achieved by inserting the hex head tool all the way into the broken screw hex through slot 4c and slowly turning the tool anti-clockwise for a complete retrieval.

The invention is not limited to a hex through slot cross section. The through slot can be of any other through cross sections, such as, for example, a triangle, a star, a polygon, a symmetrical curved opening, and an asymmetrical curved opening. The large blind hex slot is for the Allen key or hex head screwdriver used to secure the abutment screw 4 though the abutment 3 into the implant 2. The primary function of the abutment screw 4 is to provide a clamping action of the abutment 3 to the implant 2.

The abutment screw 4 has a three-prong jaw feature 4a with a short profile of external threads on the top end of the abutment screw 4. The function of the three-prong jaw feature 4a is to restrain the keying pin 5a top and prevent the keying pin 5a from rotating. The three-prong jaw feature 4a has a top edge that is chamfered, creating three small chamfered surfaces. These surfaces will be pushed inward causing a clamping action when reacting with the internal chamfer feature inside of the lock nut 5. The small section of external threads 4d below the three-pronged jaw feature 4a mate with the internal threads of the lock nut 5.

The sub-assembly 5, 5a of the dental implant system 1 comprises two separate piece parts, namely, the keying pin 5a and the lock nut 5, with one being snapped into the other. The keying pin 5a has an undercut feature at the pin top that allows the keying pin 5a to be snapped into the lock nut 5. The keying pin 5a is free to rotate with respect to the lock nut 5 after being snap into the lock nut 5. The keying pin 5a has three cylindrical portions: a top portion, a main body portion and a tip portion. The top portion of the keying pin 5a has the largest outer diameter and the surface can be with or without knurls. If it has knurls, the knurled surface provides higher frictional contact when clamped by the three-prong jaw feature 4a of the abutment screw 4. The main body portion and the tip portion of the keying pin 5a pass through the hex head 3a of the abutment 3. The centerline of the main body portion of the keying pin 5a is aligned with the top portion of the keying pin 5a with or without knurls. The tip portion of the keying pin 5a is short compared with the main body portion. The tip portion of the keying pin 5a is chamfered and has a small round to reduce contact friction. The tip portion of the keying pin 5a has a smaller diameter than the main body portion of the keying pin 5a. The centerline of the tip portion of the keying pin 5a is slightly off-centered with respect to the main body portion and the top portion of the keying pin 5a.

It should be noted that the sub-assembly 5, 5a is shown with a keying pin 5a snapped into the lock nut 5 for illustration purpose only. The keying pin 5a and lock nut 5 can be designed to make the keying pin 5a permanently captive into the lock nut 5 by swaging or other mechanical means while maintaining the rotational degree of motion with respect to the lock nut 5.

After the dental implant system 1 has been installed, when the abutment screw 4 starts to rotate, it will actuate the clamped top portion of the keying pin 5a. Any motions of the top portion of the keying pin 5a will cause the off-centered tip portion of the keying pin 5a to swing away from the initial stress-free assembled position inside the small circular blind cavity of the implant 2, thereby creating a mechanical interference with the implant 2. The clamping of the top portion of the keying pin 5a by the three-pronged jaw feature 4a of the abutment screw 4 and the mechanical interference of the tip portion of the keying pin 5a with the implant 2 serve as a positive locking mechanism for the abutment screw 4. This positive locking mechanism greatly extends the fatigue life of the abutment screw 4 by resolving the aforementioned first major dental implant issue, namely, abutment self-loosening.

The cross section of the tip portion of the keying pin 5a is not limited to a cylindrical cross section. It can be with a slight taper and of any other cross sections such as, for example, a triangle, a star, a polygon, a symmetrical closed loop, and an asymmetrical closed loop. Also, the inventive principles and concepts are also not limited to the tip portion of the keying pin 5a being off-centered from the main body portion of the keying pin 5a. The tip portion of the keying pin 5a can be aligned with the main body portion of the keying pin 5a with no offset and can have a different, non-circular cross section. The circular blind cavity of the implant 2 should match the cross section of the tip portion of the keying pin 5a. This approach will typically impact the blind-mating capability of the tip portion of the keying pin 5a into the blind cavity of the implant 2.

The lock nut 5 has a hex socket cavity for engagement with a hex head tool. A snap-on feature inside of the lock nut 5 is used for the mating of the lock nut 5 with the keying pin 5a. The lock nut 5 is equipped with an internal chamfer to achieve the closure or clamping action of the three-prong jaw feature 4a of the abutment screw 4 when tightening the lock nut 5. The lock nut 5 also has a small internal threaded section adapted to mate with the external threads 4d of the abutment screw 4. The tip portion of the keying pin 5a will continue to advance into the circular blind cavity of the implant 2 when turning the lock nut 5 clockwise. The tip portion of the keying pin 5a will stop advancing when the internal chamfer of the lock nut 5 makes contact with the chamfered surfaces of the three-pronged jaw feature 4a of the abutment screw 4.

It should be noted that the invention has been described with reference to illustrative embodiments and that the invention is not limited to these embodiments. Those with knowledge of the dental implant industry will understand the manner in which modifications can be made to the illustrative embodiments and that all such modifications are within the scope of the invention. For example, the implant 2, abutment screw 4, and the lock nut and keying pin sub-assembly 5 and 5a have been described as being used to enable tool access with a tool having a hex head feature. However, the design can be varied with different drive types. For example, the hex head though slot 4c of the abutment screw 4 can have other cross-sectional shapes. These and other modifications may be made to the embodiments described herein and all such modified embodiments are also within the scope of the invention, as will be understood by those with knowledge of the said field.

What is claimed is:

1. A dental implant system comprising:
   an implant;
   an abutment adapted to mate with the implant;
   an abutment screw having a portion that passes through the abutment and mates with the implant; and
   a sub-assembly comprising a lock nut and a keying pin, the keying pin being mechanically coupled to the lock nut and extending through the abutment screw, through the abutment and into the implant, the dental implant system providing a positive locking mechanism for the abutment screw that extends a fatigue life of the abutment screw.

2. The dental implant system of claim 1, further comprising:
   a retrieval feature formed in the abutment screw that allows the abutment screw to be easily retrieved from the implant in the event that the abutment screw becomes damaged.

3. The dental implant system of claim 1, wherein the implant has an internal chamfer feature below internal threads of a tap drill hole of the abutment; the internal chamfer feature serving as a guiding surface for a tip portion of the keying pin to allow the tip portion to self-rotate into a circular blind cavity of the implant that is under the internal chamfer feature.

4. The dental implant system of claim 3, wherein the circular blind cavity of the implant is off-centered with respect to the internal chamfer feature of the implant and with respect to the tap drill hole.

5. The dental implant system of claim 4, wherein the circular blind cavity that is aligned with the tip portion of the keying pin.

6. The dental implant system of claim 5, wherein the retrieval feature comprises a through slot that allows the abutment screw to be easily retrieved from inside of the implant with the use of a simple tool in the event that the abutment screw is broken.

7. The dental implant system of claim 6, wherein the through slot is a hex through slot adapted to receive an end of a hex head drive tool.

8. The dental system of claim 7, wherein the abutment screw is equipped with a jaw feature adapted to restrain or clamp the keying pin and a small threaded section for mating with the lock nut.

9. The dental implant system of claim 8, wherein a clamping of a top portion of the keying pin by the jaw feature of the abutment screw and the off-centered tip portion of the keying pin reacting with the circular blind cavity of the implant provides the positive locking mechanism for the abutment screw, and wherein the positive locking mechanism prevents self-loosening of the abutment screw.

10. The dental system of claim 8, wherein the jaw feature is a three-prong jaw feature that is chamfered and that is adapted to close when reacting with an internal chamfer of the lock nut.

11. The dental implant system of claim 10, wherein the keying pin snaps into the lock nut and is free to rotate with respect to the lock nut after the keying pin has been snapped into the lock nut.

12. The dental implant system of claim 11, wherein the lock nut has a short internal threaded section for mating with external threads of the abutment screw that are adjacent the jaw.

13. The dental system of claim 1, wherein the implant has a female Morse Taper cavity, and wherein the abutment has a Morse Taper male portion that mates with the female Morse Taper cavity in an interference fit when the abutment screw is tightened, and wherein the mating of the Morse Taper male portion with the female Morse Taper cavity in the interference fit restrains the abutment from axial and rotational movements relative to the implant.

14. The dental system of claim 13, wherein the mating of the Morse Taper male portion with the female Morse Taper cavity in the interference fit provides a hermetic seal that prevents growth of bacteria at a crevice between the implant and the abutment.

15. A dental implant system comprising:
an implant;
an abutment adapted to mate with the implant;
an abutment screw having a portion that passes through the abutment and mates with the implant, the abutment screw having a retrieval feature; and
a sub-assembly comprising a lock nut and a keying pin, the keying pin being mechanically coupled to the lock nut and extending through the abutment screw, through the abutment and into the implant, the dental implant system providing a positive locking mechanism for the abutment screw that extends a fatigue life of the abutment screw, and wherein the retrieval feature of the abutment screw allows the abutment screw to be easily retrieved from the implant in the event that the abutment screw becomes damaged.

16. The dental implant system of claim 15, wherein the implant has an internal chamfer feature below internal threads of a tap drill hole of the abutment; the internal chamfer feature serving as a guiding surface for a tip portion of the keying pin to allow the tip portion to self-rotate into a circular blind cavity of the implant that is under the internal chamfer feature.

17. The dental implant system of claim 16, wherein the circular blind cavity of the implant is off-centered with respect to the internal chamfer feature of the implant and with respect to the tap drill hole.

18. The dental implant system of claim 17, wherein the abutment screw is equipped with a jaw feature adapted to restrain or clamp the keying pin and a small threaded section for mating with the lock nut, wherein a clamping of a top portion of the keying pin by the jaw feature of the abutment screw and the tip portion of the keying pin being off-centered and reacting with the circular blind cavity of the implant provides the positive locking mechanism for the abutment screw, and wherein the positive locking mechanism prevents self-loosening of the abutment screw.

19. The dental system of claim 18, wherein the jaw feature is a three-prong jaw feature that is chamfered and that is adapted to close when reacting with an internal chamfer of the lock nut.

20. The dental implant system of claim 15, wherein the retrieval feature comprises a through slot that allows the abutment screw to be easily retrieved from inside of the implant with the use of a simple tool in the event that the abutment screw is broken.

* * * * *